(12) United States Patent
Yip (10) Patent No.: US 12,370,000 B2
(45) Date of Patent: Jul. 29, 2025

(54) REAR-END TRANSMISSION DEVICE, SURGICAL INSTRUMENT, AND SURGICAL ROBOT

(71) Applicant: CORNERSTONE TECHNOLOGY (SHENZHEN) LIMITED, Guangdong (CN)

(72) Inventor: Hoiwut Yip, Guangdong (CN)

(73) Assignee: CORNERSTONE TECHNOLOGY (SHENZHEN) LIMITED, Shenzhen (CN)

(*) Notice: Subject to any disclaimer, the term of this patent is extended or adjusted under 35 U.S.C. 154(b) by 172 days.

(21) Appl. No.: 18/496,608

(22) Filed: Oct. 27, 2023

(65) Prior Publication Data
US 2024/0050174 A1 Feb. 15, 2024

Related U.S. Application Data

(63) Continuation of application No. PCT/CN2022/078978, filed on Mar. 3, 2022.

(30) Foreign Application Priority Data

Apr. 30, 2021 (CN) .......................... 202110484496.4

(51) Int. Cl.
*A61B 34/30* (2016.01)
*A61B 34/00* (2016.01)

(52) U.S. Cl.
CPC .............. *A61B 34/30* (2016.02); *A61B 34/71* (2016.02); *A61B 34/74* (2016.02)

(58) Field of Classification Search
CPC ......... A61B 34/30; A61B 34/71; A61B 34/74; A61B 2034/305; A61B 2034/306
See application file for complete search history.

(56) References Cited

U.S. PATENT DOCUMENTS

| | | | | |
|---|---|---|---|---|
| 5,912,658 A | * | 6/1999 | Bergamasco | .......... B25J 9/0006 600/595 |
| 8,821,480 B2 | * | 9/2014 | Burbank | ................ A61B 34/30 606/1 |

(Continued)

FOREIGN PATENT DOCUMENTS

| CN | 112043389 A | 12/2020 |
|---|---|---|
| CN | 112043391 A | 12/2020 |

(Continued)

OTHER PUBLICATIONS

Cornerstone Technology (Shenzhen) Limited, Extended European Search Report, EP 22794333.9, Aug. 19, 2024, 23 pgs.

(Continued)

*Primary Examiner* — Ryan J. Severson
(74) *Attorney, Agent, or Firm* — USCH Law, PC (57) ABSTRACT

A rear-end transmission device, a surgical instrument, and a surgical robot are provided. The rear-end transmission device includes a first rotating member, a second rotating member, a first pulley assembly, a second pulley assembly, and a position adjusting assembly. The first rotating member is connected to a first cable and a second cable. The second rotating member is connected to a third cable and a fourth cable. The first pulley assembly includes a first movable pulley. The second pulley assembly includes a second movable pulley. The position adjusting assembly is configured to concurrently adjust positions of the first movable pulley and the second movable pulley, to pull in the first cable and the second cable while releasing the third cable and the fourth cable, or to pull in the third cable and the fourth cable while releasing the first cable and the second cable.

20 Claims, 6 Drawing Sheets

(56) References Cited

U.S. PATENT DOCUMENTS

| | | | | |
|---|---|---|---|---|
| 2008/0216596 | A1* | 9/2008 | Madhani | B25J 9/104 901/26 |
| 2010/0011901 | A1 | 1/2010 | Burbank | |
| 2013/0090194 | A1* | 4/2013 | Ferlay | B25J 9/104 474/73 |
| 2019/0192242 | A1* | 6/2019 | Xu | A61B 17/00 |
| 2019/0328467 | A1* | 10/2019 | Waterbury | A61B 34/30 |
| 2023/0380918 | A1* | 11/2023 | Wang | A61B 34/37 |
| 2024/0050174 | A1* | 2/2024 | Yip | A61B 34/74 |
| 2024/0051120 | A1* | 2/2024 | Yip | B25J 9/104 |
| 2025/0152286 | A1* | 5/2025 | Sun | A61B 34/71 |

FOREIGN PATENT DOCUMENTS

| | | |
|---|---|---|
| CN | 112274251 A | 1/2021 |
| CN | 112370173 A | 2/2021 |
| CN | 112402021 A | 2/2021 |
| CN | 112539256 A | 3/2021 |
| CN | 213641171 U | 7/2021 |
| CN | 113367796 A | 9/2021 |
| JP | 2000014628 A | 1/2000 |

OTHER PUBLICATIONS

Cornerstone Technology (Shenzhen) Limited, International Search Report with English translation, PCT/CN2022/078978, May 19, 2022, 6 pgs.

* cited by examiner

REAR-END TRANSMISSION DEVICE, SURGICAL INSTRUMENT, AND SURGICAL ROBOT

CROSS REFERENCE TO RELATED APPLICATIONS

This application is a continuation of PCT Patent Application No. PCT/CN2022/078978, filed Mar. 3, 2022, which claims priority to Chinese Patent Application No. CN202110484496.4, filed on Apr. 30, 2021, each of which is hereby incorporated by reference in its entirety.

TECHNICAL FIELD

The various embodiments described in this document relate in general to the technical field of medical devices, and more specifically to a rear-end transmission device, a surgical instrument, and a surgical robot.

BACKGROUND

In robot-assisted minimally invasive surgery, surgical instruments connected at the end of the robot enter the human body through wounds on the surface of the human body or natural canals of the human body, to be operated on tissues in the human body. The surgical instrument mainly includes an effector or tool (such as a pair of surgical forceps, a cutting tool, or a cauterizing tool) mounted to a wrist mechanism at a front end of the instrument, the wrist mechanism providing multiple degrees of freedom for movement of the front end, a main shaft extending from a rear end of the instrument to the front end, and a power and transmission device at the rear end of the instrument. The effector at the front end and the wrist mechanism are generally driven by multiple cables fixed thereto, and the cables run through the main shaft of the surgical instrument and are driven by the power and transmission device at the rear end.

For surgical forceps and other holding or cutting tools, the wrist mechanism is generally required to realize three degrees of freedom: pitch, yaw, and grip. Cooperated with extra degrees of freedom of the rear end of the robot, the wrist mechanism can realize the movement required to perform surgical operations. According to specific implementation of the wrist mechanism, the number of driving cables required for the wrist mechanism varies, for example, there are generally 4 or 6 cables configured for the wrist mechanism. In addition, in order to realize a large-scale movement (for example, rotation of −90° to 90°) of each joint of the wrist mechanism, it is necessary to arrange extra pulleys on the wrist mechanism to guide cables. However, addition of the extra pulleys may hinder the miniaturization of the front end of the surgical instrument, and the use of more cables may also increase the size and cost of the instrument.

The existing rear-end transmission device for driving the 4-cable wrist mechanism realizes release of two cables and pulling in of other two cables through swing of a connecting rod or a rocker arm, thereby realizing the pitch of the wrist mechanism. In this way, with the change of a pitch angle, a length of a pulled-in cable is not equal to a length of a released cable, which may lead to a change in tension of the cables, and then lead to problems such as reduced accuracy due to a transmission error caused by loosened cables, or accelerated wear due to excessive frictional resistance caused by over-tensioned cables. To avoid such problems, one method is to limit a range of a rotation angle of a pitch joint, but this method may affect the function of the instrument. In addition, when using this mechanism, a rotation angle of an output terminal of the motor at the rear end has a nonlinear relationship with the pitch angle of the wrist mechanism, which requires extra calibration to achieve accurate position control and thus increases extra workload.

SUMMARY

A series of simplified concepts have been introduced in this section, which will be further elaborated in the detailed description. The section of the disclosure does not mean attempting to limit key features and essential technical features of the claimed technical solution, nor does it mean attempting to determine the scope of protection of the claimed technical solution.

Embodiments of the disclosure provide a rear-end transmission device and includes a first rotating member, a second rotating member, a first pulley assembly, a second pulley assembly, and a position adjusting assembly. The first rotating member is connected to a first cable and a second cable, where the first cable and the second cable wrap around the first rotating member in opposite directions. The second rotating member is connected to a third cable and a fourth cable, where the third cable and the fourth cable wrap around the second rotating member in opposite directions. The first pulley assembly includes a first movable pulley, where each of the first cable and the second cable extends from the first rotating member and rides on the first movable pulley. The second pulley assembly includes a second movable pulley, where each of the third cable and the fourth cable extends from the second rotating member and rides on the second movable pulley. The position adjusting assembly is connected to the first movable pulley and the second movable pulley, and configured to concurrently adjust positions of the first movable pulley and the second movable pulley, to pull in the first cable and the second cable while releasing the third cable and the fourth cable, or to pull in the third cable and the fourth cable while releasing the first cable and the second cable.

According to an embodiment of the present disclosure, the rear-end transmission device is connected to four driving cables of the wrist mechanism, such that the wrist mechanism works cooperatively with the rear-end transmission device to achieve pitch, yaw, and grip of the wrist mechanism by pulling in or releasing the driving cables, which is simple in structure and accurate in transmission. In addition, a rotation angle of the rotating member is linearly related to a pitch angle, a yaw angle, or a grip angle of the wrist mechanism, and therefore, equal-length release and/or pulling-in of the driving cables can be ensured even when the above-mentioned angles of the wrist mechanism vary in a wide range.

In some embodiments, the first rotating member is rotatable around a first central axis of the first rotating member to perform via the first pulley assembly: pulling in one of the first cable and the second cable while releasing another of the first cable and the second cable; and the second rotating member is rotatable around a second central axis of the second rotating member to perform via the second pulley assembly: pulling in one of the third cable and the fourth cable while releasing another of the third cable and the fourth cable.

In some embodiments, the first central axis is substantially parallel to the second central axis, each of the first movable pulley and the second movable pulley is rotatable around a respective axis substantially parallel to the first central axis, and the axis of the first movable pulley and the axis of the second movable pulley are spaced apart from each other.

In some embodiments, the first pulley assembly further includes a first guide pulley and a third guide pulley, each of the first guide pulley and the third guide pulley is rotatable around a respective axis substantially parallel to the first central axis, and each of the first cable and the second cable extends from the first rotating member and sequentially rides on the first guide pulley, the first movable pulley, and the third guide pulley.

In some embodiments, the second pulley assembly further includes a second guide pulley and a fourth guide pulley, each of the second guide pulley and the fourth guide pulley is rotatable around a respective axis substantially parallel to the second central axis, and each of the third cable and the fourth cable extends from the second rotating member and sequentially rides on the second guide pulley, the second movable pulley, and the fourth guide pulley.

In some embodiments, the position adjusting assembly includes a third rotating member, and the third rotating member is rotatable around a third central axis of the third rotating member substantially parallel to the first central axis, to concurrently adjust the positions of the first movable pulley and the second movable pulley.

In some embodiments, the position adjusting assembly further includes a slider, each of the first movable pulley and the second movable pulley is rotatably connected to the slider, and the third rotating member is configured to directly or indirectly adjust a position of the slider.

In some embodiments, the position adjusting assembly further includes a first transmission cable, a second transmission cable, a fifth guide pulley, and a sixth guide pulley. The first transmission cable rides on the fifth guide pulley; and the second transmission cable rides on the sixth guide pulley, where the first transmission cable and the second transmission cable each have one end connected to the third rotating member and wrap around the third rotating member in opposite directions, and the first transmission cable has another end connected to one end of the slider and the second transmission cable has another end connected to another end of the slider.

In some embodiments, the fifth guide pulley and the sixth guide pulley each are rotatable around a respective axis substantially parallel to the third central axis, and the axis of the fifth guide pulley and the axis of the sixth guide pulley are spaced apart from each other.

In some embodiments, the position adjusting assembly further includes a first transmission cable, a second transmission cable, and a rotating assembly. The first transmission cable and the second transmission cable each have one end connected to the third rotating member and wrap around the third rotating member in opposite directions; the first transmission cable and the second transmission cable each have another end connected to the rotating assembly and wrap around the rotating assembly in opposite directions; and the rotating assembly is meshed with the slider, and the slider is linearly movable with a rotation of the rotating assembly.

In some embodiments, the rotating assembly is rotatable around an axis substantially parallel to the third central axis, the rotating assembly includes a gear, and the slider is a rack meshed with the gear.

In some embodiments, the position adjusting assembly includes a pair of substantially parallel sliders, each of the first movable pulley and the second movable pulley is rotatably connected to a respective one of the pair of sliders, and the rotating assembly is disposed between the pair of sliders and is meshed with the pair of sliders, to enable the pair of sliders to move in opposite directions.

Embodiments of the disclosure further provide a surgical instrument including the rear-end transmission device described in any embodiment of the disclosure.

Embodiments of the disclosure further provide a surgical robot including the surgical instrument described in any embodiment of the disclosure.

BRIEF DESCRIPTION OF THE DRAWINGS

The following drawings of the disclosure are herein used as a part of the disclosure for understanding the disclosure. Embodiments of the present disclosure are described with reference to the accompanying drawings to explain the principles of the present disclosure, in which.

DETAILED DESCRIPTION OF THE EMBODIMENTS

Detailed illustration is given in the following description to provide a more thorough understanding of the disclosure. However, it will be apparent to those skilled in the art that embodiments of the present disclosure may be practiced without one or more of these details. In other examples, some technical features well known in the art are not described in order to avoid confusion with embodiments of the present disclosure.

In order to fully understand the embodiments of the present disclosure, detailed structures will be set forth in the following description. Apparently, the implementation of the embodiments of the present disclosure is not limited to particular details familiar to those skilled in the art. It is to be noted that ordinal numbers such as "first" and "second" referenced in the disclosure are merely identifiers and do not have any other meaning, e.g., does not represent a specific order. In addition, for example, the term "first component/member" does not imply the existence of a "second component/member", and the term "second component/member" does not imply the existence of the "first component/member". The terms "up", "down", "front", "back", "left", "right", and similar expressions used in the disclosure are merely intended to explain the disclosure rather than limit the disclosure.

Embodiments of the present disclosure provide a rear-end transmission device, a surgical instrument, and a surgical robot. The surgical robot includes a movable robotic arm and a surgical instrument mounted to the robotic arm. The surgical instrument includes the rear-end transmission device. As known in the art, the surgical instrument can achieve a number of functions and includes but is not limited to a pair of surgical forceps or grippers of different shapes and sizes, a needle driver, a pair of scissors, or a cauterizing tool.

Embodiment 1

A surgical robot 100 according to the first embodiment of the present disclosure will be described in detail below with reference to FIGS. 1 to 3.

Figure 1:
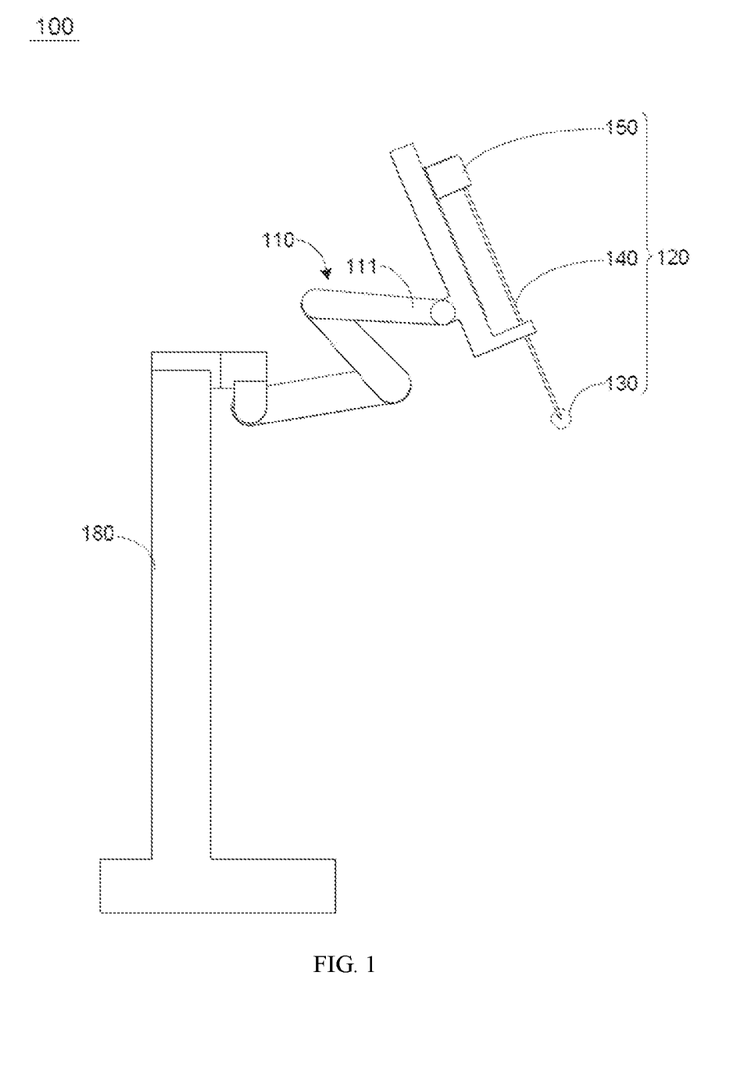
FIG. 1 is a schematic structural view of a surgical robot according to a first embodiment of the present disclosure.

As shown in FIG. 1, the surgical robot 100 mainly includes a base 180, at least one robotic arm 110 rotatably disposed at an upper end of the base 180, and at least one surgical instrument 120. Each surgical instrument 120 is mounted to a port of a respective robotic arm 110. Merely one robotic arm 110 is exemplarily shown in FIG. 1, the robotic arm 110 includes a plurality of links 111 connected sequentially, and each of the plurality of links 111 is rotatable. In a case where the surgical robot 100 includes multiple robotic arms 110, each robotic arm 110 is provided with a respective surgical instrument 120 which is mounted to a port of the robotic arm 110. Each surgical instrument 120 is detachably coupled to the respective robotic arm 110, to facilitate replacement or repairment of the surgical instrument 120. Therefore, the surgical instrument 120 mounted to the respective robotic arm 110 may be used for a particular medical procedure or may be changed during the medical procedure to provide a desired clinical function.

The robotic arm 110 includes at least one docking port. The at least one docking port generally includes an output of a driving motor configured to provide mechanical power for operation of the surgical instrument 120. The at least one docking port may further include an electrical interface to which the surgical instrument 120 is coupled, to identify a type of a device coupled to the docking port and to obtain parameters of the device.

The surgical instrument 120 generally includes the rear-end transmission device 150, a main shaft 140 extending from the rear-end transmission device 150, and a wrist mechanism 130 at a distal end of the main shaft 140. Driving cables (specifically including a first cable 141, a second cable 142, a third cable 143, and a fourth cable 144) and an electrical conductor that are connected to the wrist mechanism 130 run through the main shaft 140 and are connected to the rear-end transmission device 150. The rear-end transmission device 150 is configured to provide mechanical coupling between the above-described driving cables and a motor driving shaft of the driving motor, so as to operate the wrist mechanism 130 by controlling movement and tension of the driving cables. The main shaft 140 is hollow and may be rigid or flexible.

Figure 2:
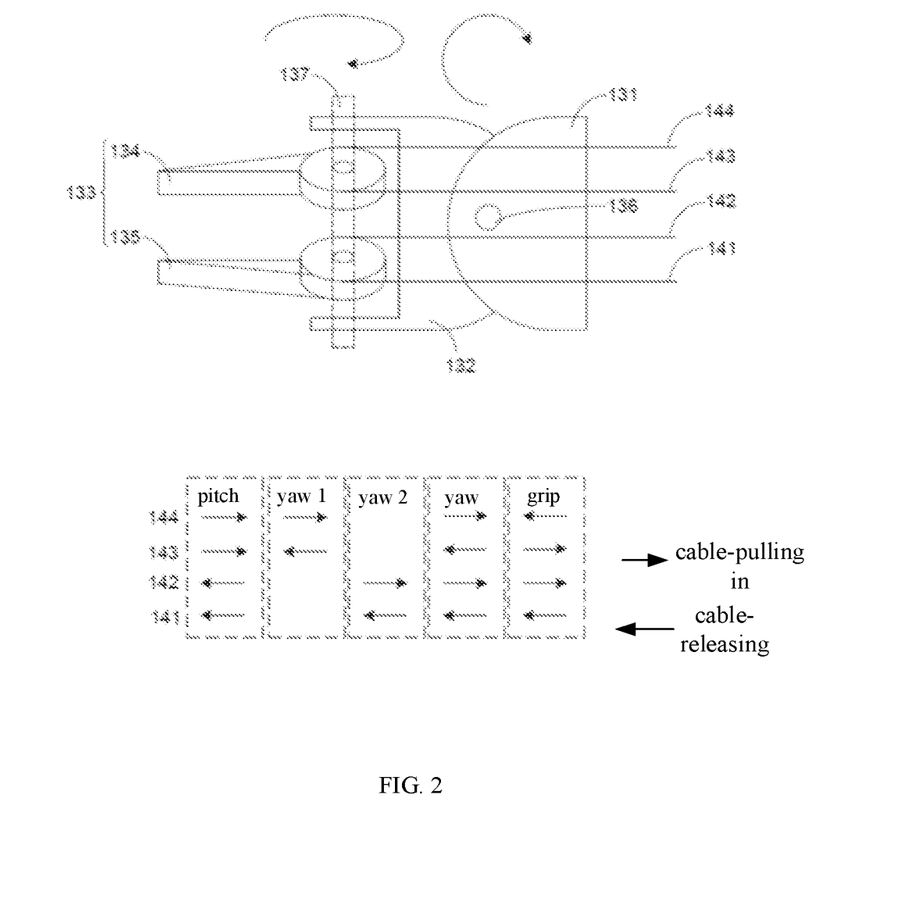
FIG. 2 is a schematic partial structural view of the surgical robot of FIG. 1 including a wrist mechanism, a first cable, a second cable, a third cable, and a fourth cable.

As shown in FIG. 2, the wrist mechanism 130 includes a proximal clevis 131, a distal clevis 132, and an effector 133. The distal clevis 132 is pivotably connected to the proximal clevis 131 via a first bolt 136, such that pitch of the wrist mechanism 130 is realized through rotation of the distal clevis 132 relative to the proximal clevis 131. The effector 133 includes an upper claw 134 and a lower claw 135. Each of the upper claw 134 and the lower claw 135 is pivotably connected to the distal clevis 132 via a second bolt 137, such that grip and yaw of the wrist mechanism 130 are realized through rotation of the claws 134, 135 relative to the distal clevis 132. In some embodiments, the second bolt 137 is substantially perpendicular to the first bolt 136. Alternatively, the second bolt 137 may not be perpendicular to the first bolt 136 as desired.

The first cable 141 and the second cable 142 are attached to the lower claw 135 of the effector 133 and each are wound at least half a turn. The third cable 143 and the fourth cable 144 are attached to the upper claw 134 of the effector 133 and each are wound at least half a turn. The first cable 141, the second cable 142, the third cable 143, and the fourth cable 144 are extended along hard surfaces of guide passages (not shown) defined by the effector 133, the distal clevis 132, and the proximal clevis 131, and then reach the rear-end transmission device 150 along the main shaft 140. The guide passage may be a groove having a U-shaped or semicircular cross section.

Continuing with reference to FIG. 2, by pulling in the third cable 143 and the fourth cable 144 in equal lengths while releasing the first cable 141 and the second cable 142 in equal lengths, the distal clevis 132 is rotated clockwise around the first bolt 136 relative to the proximal clevis 131, to achieve pitch of the wrist mechanism 130 in a direction (referring to FIG. 2). Similarly, by pulling in the first cable 141 and the second cable 142 in equal lengths while releasing the third cable 143 and the fourth cable 144 in equal lengths, the distal clevis 132 is rotated counterclockwise around the first bolt 136 relative to the proximal clevis 131, to achieve pitch of the wrist mechanism 130 in a reverse direction.

The upper claw 134 is rotated clockwise around the second bolt 137 relative to the distal clevis 132 by pulling in the fourth cable 144 and releasing the third cable 143 concurrently in equal lengths (referring to yaw 1 in FIG. 2). Similarly, the upper claw 134 is rotated counterclockwise around the second bolt 137 relative to the distal clevis 132 by pulling in the third cable 143 and releasing the fourth cable 144 concurrently in equal lengths. The lower claw 135 is rotated clockwise around the second bolt 137 relative to the distal clevis 132 by pulling in the second cable 142 and releasing the first cable 141 concurrently in equal lengths (referring to yaw 2 in FIG. 2). Similarly, the lower claw 135 is rotated counterclockwise around the second bolt 137 relative to the distal clevis 132 by pulling in the first cable 141 and releasing the second cable 142 concurrently in equal lengths. The effector 133 can achieve yaw and grip through aggregate motion of the upper claw 134 and the lower claw 135, which is described in detail below.

Figure 3:
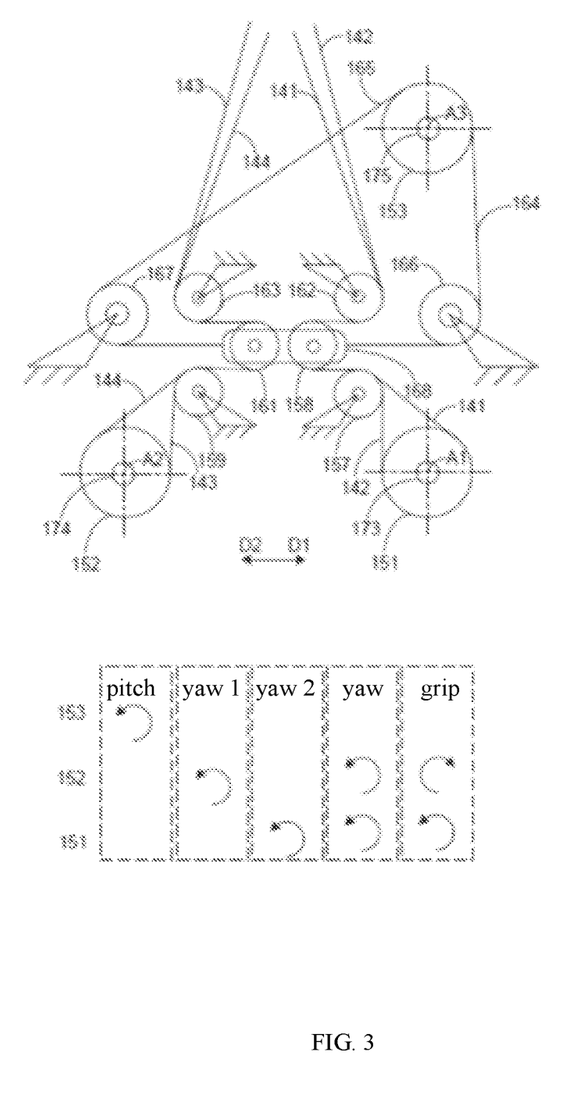
FIG. 3 is another schematic partial structural view of the surgical robot of FIG. 1 including a rear-end transmission device.

As shown in FIG. 3, the rear-end transmission device 150 mainly includes a first rotating member 151, a second rotating member 152, a first pulley assembly, a second pulley assembly, a position adjusting assembly, a first rotating shaft 173, a second rotating shaft 174, and a third rotating shaft 175. Each of the first rotating shaft 173, the second rotating shaft 174, and the third rotating shaft 175 is connected to a respective driving motor at a respective docking port of the robotic arm 110. The robotic arm 110 may be provided with at least three driving motors each being mounted to a respective docking port. The three driving motors are connected to the first rotating shaft 173, the second rotating shaft 174, and the third rotating shaft 175, respectively. The first rotating shaft 173, the second rotating shaft 174, and the third rotating shaft 175 are arranged substantially parallel to each other. The first rotating shaft 173, the second rotating shaft 174, and the third rotating shaft 175 are arranged at three tips of a substantial triangle. It shall be understood that there is no restriction on arrangement of the first rotating shaft 173, the second rotating shaft 174, and the third rotating shaft 175. The first rotating shaft 173, the second rotating shaft 174, and the third rotating shaft 175 may also be arranged in a straight line as required. The position adjusting assembly further includes a third rotating member 153. The first rotating shaft 173 is fixedly connected to the first rotating member 151 to drive rotation of the first rotating member 151. The second rotating shaft 174 is fixedly connected to the second rotating member 152 to drive rotation of the second rotating member 152. The third rotating shaft 175 is fixedly connected to the third rotating member 153, to drive rotation of the third rotating member 153.

The first rotating member 151 is connected to the first cable 141 and the second cable 142. The first cable 141 and the second cable 142 wrap around the first rotating member 151 in opposite directions. The second rotating member 152 is connected to the third cable 143 and the fourth cable 144. The third cable 143 and the fourth cable 144 wrap around the second rotating member 152 in opposite directions. In embodiments of the disclosure, each of the first rotating member 151 and the second rotating member 152 is a winch.

The first pulley assembly includes a first guide pulley1 57, a first movable pulley 158, and a third guide pulley 162. Each of the first cable 141 and the second cable 142 extends from the first rotating member 151 and rides on the first guide pulley 157, the first movable pulley 158, and the third guide pulley 162 sequentially. The first rotating member 151 is rotatable around a first central axis A1 of the first rotating member 151 to be able to perform via the first pulley assembly: pulling in one of the first cable 141 and the second cable 142 and releasing the other of the first cable 141 and the second cable 142 in equal lengths concurrently, to achieve clockwise or counterclockwise rotation of the lower claw 135 relative to the distal clevis 132 around the second bolt 137. In an embodiment, each of the first guide pulley1 57, the first movable pulley 158, and the third guide pulley 162 is rotatable around a respective axis substantially parallel to the first central axis A1. The axis of the first guide pulley1 57, the axis of the first movable pulley 158, and the axis of the third guide pulley 162 are spaced apart from one another. Each of the first guide pulley 157 and the third guide pulley 162 is a fixed pulley.

Specifically, during stationary of the first movable pulley 158, when the first rotating shaft 173 is controlled by the driving motor to drive the first rotating member 151 to rotate counterclockwise, the second cable 142 is pulled in for a length and the first cable 141 is released for the length concurrently, thereby realizing the clockwise rotation of the lower claw 135 relative to the distal clevis 132 around the second bolt 137 (see yaw 2 in FIG. 2). During stationary of the first movable pulley 158, when the first rotating shaft 173 is controlled by the driving motor to drive the first rotating member 151 to rotate clockwise, the first cable 141 is pulled in and the second cable 142 is released in equal lengths concurrently, thereby realizing the counterclockwise rotation of the lower claw 135 relative to the distal clevis 132 around the second bolt 137.

The second pulley assembly includes a second guide pulley 159, a second movable pulley 161, and a fourth guide pulley 163. Each of the third cable 143 and the fourth cable 144 extends from the second rotating member 152 and rides on the second guide pulley 159, the second movable pulley 161, and the fourth guide pulley 163 sequentially. The second rotating member 152 is rotatable around a second central axis A2 of the second rotating member 152 to be able to perform via the second pulley assembly: pulling in one of the third cable 143 and the fourth cable 144 and releasing the other of the third cable 143 and the fourth cable 144 in equal lengths concurrently, to achieve clockwise or counterclockwise rotation of the upper claw 134 relative to the distal clevis 132 around the second bolt 137. In an embodiment, the first central axis A1 is substantially parallel to the second central axis A2. Each of the second guide pulley 159, the second movable pulley 161, and the fourth guide pulley 163 is rotatable around a respective axis substantially parallel to the second central axis A2. The axis of the second guide pulley 159, the axis of the second movable pulley 161, and the axis of the fourth guide pulley 163 are spaced apart from one another. The second guide pulley 159 and the fourth guide pulley 163 each are a fixed pulley.

Specifically, during stationary of the second movable pulley 161, when the second rotating shaft 174 is controlled by the driving motor to drive the second rotating member 152 to rotate counterclockwise, the fourth cable 144 is pulled in and the third cable 143 is released in equal lengths concurrently, so that the upper claw 134 rotates clockwise around the second bolt 137 with respect to the distal clevis 132 (referring to yaw 1 in FIG. 2). During stationary of the second movable pulley 161, when the second rotating shaft 174 is controlled by the driving motor to drive the second rotating member 152 to rotate clockwise, the third cable 143 is pulled in and the fourth cable 144 is released in equal lengths concurrently, so that the upper claw 134 rotates counterclockwise around the second bolt 137 relative to the distal clevis 132.

In embodiments of the disclosure, by controlling rotation of the first rotating shaft 173 and the second rotating shaft 174, yaw and grip of the effector 133 can be realized.

Specifically, when both the first rotating shaft 173 and the second rotating shaft 174 rotate counterclockwise at equal angles, that is, when both the first rotating member 151 and the second rotating member 152 rotate counterclockwise at equal angles, both the upper claw 134 and the lower claw 135 rotate clockwise, thereby realizing yaw of the effector 133 in a direction (referring to FIG. 2). When both the first rotating shaft 173 and the second rotating shaft 174 rotate clockwise at equal angles, that is, when both the first rotating member 151 and the second rotating member 152 rotate clockwise at equal angles, both the upper claw 134 and the lower claw 135 rotate counterclockwise, thereby realizing yaw of the effector 133 in a reverse direction.

When the first rotating shaft 173 rotates counterclockwise and the second rotating shaft 174 rotates clockwise concurrently at equal angles, that is, when the first rotating member 151 rotates counterclockwise and the second rotating member 152 rotates clockwise concurrently at equal angles, the lower claw 135 rotates clockwise and the upper claw 134 rotates counterclockwise, to realize grip of the effector 133 (referring to FIG. 2). When the first rotating shaft 173 rotates clockwise and the second rotating shaft 174 rotates counterclockwise at equal angles concurrently, that is, when the first rotating member 151 rotates clockwise and the second rotating member 152 rotates counterclockwise concurrently at equal angles, the lower claw 135 rotates counterclockwise and the upper claw 134 rotates clockwise, to realize releasing of the grip of the effector 133.

The position adjusting assembly is connected to the first movable pulley 158 and the second movable pulley 161, and is configured to concurrently adjust positions of the first movable pulley 158 and the second movable pulley 161, so as to pull in the first cable 141 and the second cable 142 in equal lengths while releasing the third cable 143 and the fourth cable 144 in equal lengths, or to pull in the third cable 143 and the fourth cable 144 in equal lengths while releasing the first cable 141 and the second cable 142 in equal lengths. Therefore, the distal clevis 132 rotates counterclockwise or clockwise around the first bolt 136 relative to the proximal clevis 131 to achieve pitch of the wrist mechanism 130.

As described above, the position adjusting assembly further includes the third rotating member 153. The third rotating member 153 is rotatable around a third central axis A3, of the third rotating member 153, substantially parallel to the first central axis A1, to concurrently adjust the positions of the first movable pulley 158 and the second movable pulley 161. In embodiments of the disclosure, the third rotating member 153 is a winch.

The position adjusting assembly further includes a slider 168. The slider 168 may be configured as a strip-shaped plate. The first movable pulley 158 and the second movable pulley 161 each mounted to the slider 168 via a respective rotating shaft, such that each of the first movable pulley 158 and the second movable pulley 161 is rotatably connected to the slider 168. The first movable pulley 158 and the second movable pulley 161 are spaced apart from each other and provided on a same side of the slider 168. In an embodiment, the rotating shaft of the first movable pulley 158 is substantially parallel to the rotating shaft of the second movable pulley 161 and is substantially perpendicular to the slider 168. The third rotating member 153 can directly or indirectly adjust a position of the slider 168.

The position adjusting assembly further includes a first transmission cable 164, a second transmission cable 165, a fifth guide pulley 166, and a sixth guide pulley 167. The first transmission cable 164 rides on the fifth guide pulley 166, and the second transmission cable 165 rides on the sixth guide pulley 167. The first transmission cable 164 and the second transmission cable 165 each have one end connected to the third rotating member 153 and wrap around the third rotating member 153 in opposite directions. The first transmission cable 164 has the other end connected to one end of two opposite ends of the slider 168, and the second transmission cable 165 has the other end connected to the other end of the two opposite of the slider 168. In an embodiment, each of the fifth guide pulley 166 and the sixth guide pulley 167 is rotatable around a respective axis substantially parallel to the third central axis A3, and the axis of the fifth guide pulley 166 and the axis of the sixth guide pulley 167 are spaced apart from each other. The fifth guide pulley 166 and the sixth guide pulley 167 each may be a fixed pulley.

The fifth guide pulley 166 and the sixth guide pulley 167 serve as guides for the cables, such that a portion of the first transmission cable 164 located between the fifth guide pulley 166 and the slider 168 is substantially parallel to a portion of the second transmission cable 165 located between the sixth guide pulley 167 and the slider 168 and substantially parallel to a moving direction of the slider 168. The arrows in FIG. 3 show moving directions D1 and D2 of the slider 168, where the moving direction D2 is opposite to the moving direction D1. In an embodiment, the moving directions D1 and D2 of the slider 168 are substantially horizontal. It shall be understood that the moving direction of the slider 168 may be selected as required. For example, the moving directions D1 and D2 of the slider 168 may also be substantially vertical or may also be at an angle with the horizontal.

In one embodiment, the portion of the first transmission cable 164 located between the fifth guide pulley 166 and the slider 168 and the portion of the second transmission cable 165 located between the sixth guide pulley 167 and the slider 168 are arranged in a same straight line. It shall be understood that additional guide pulleys may be employed as needed to guide the first transmission cable 164 and the second transmission cable 165.

Furthermore, in an embodiment, the first guide pulley 157 and the third guide pulley 162 are configured to guide the first cable 141 and the second cable 142, such that a portion of each respective cable of the first cable 141 and the second cable 142 located between the first guide pulley 157 and the first movable pulley 158 is substantially parallel to a portion of the respective cable of the first cable 141 and the second cable 142 located between the first movable pulley 158 and the third guide pulley 162. The second guide pulley 159 and the second movable pulley 161 are configured to guide the third cable 143 and the fourth cable 144, so that a portion of each respective cable of the third cable 143 and the fourth cable 144 located between the second guide pulley 159 and the second movable pulley 161 is substantially parallel to a portion of the respective cable of the third cable 143 and the fourth cable 144 located between the second movable pulley 161 and the fourth guide pulley 163. Therefore, when the first movable pulley 158 and the second movable pulley 161 move with the slider 168, the first cable 141, the second cable 142, the third cable 143, and the fourth cable 144 apply no additional force and torque to the slider 168 except the forces in the moving direction of the slider 168 and the torques caused by the forces. It shall be understood that additional guide pulleys may be employed as needed to guide the first cable 141, the second cable 142, the third cable 143, and the fourth cable 144.

Specifically, when the third rotating shaft 175 is controlled by the driving motor to drive the third rotating member 153 to rotate counterclockwise, the first transmission cable 164 is pulled in and the second transmission cable 165 is released in equal lengths concurrently, to pull the slider 168, the first movable pulley 158, and the second movable pulley 161 to move in the direction D1. Therefore, the first cable 141 and the second cable 142 are released in equal lengths and the third cable 143 and the fourth cable 144 are pulled in in equal lengths concurrently, where a total length of released portions of the first cable and the second cable is equal to a total length of pulled-in portions of the third cable and the fourth cable, thereby realizing the pitch of the wrist mechanism 130 in a direction. Similarly, when the third rotating shaft 175 is controlled by the driving motor to drive the third rotating member 153 to rotate clockwise, the first transmission cable 164 is released and the second transmission cable 165 is pulled in in equal lengths concurrently, to pull in the slider 168, the first movable pulley 158, and the second movable pulley 161 to move in the direction D2. Therefore, the first cable 141 and the second cable 142 are pulled in in equal lengths and the third cable 143 and the fourth cable 144 are released in equal lengths concurrently, where a total length of pulled-in portions of the first cable and the second cable is equal to a total length of released portions of the third cable and the fourth cable, thereby realizing the pitch of the wrist mechanism 130 in a reverse direction.

Second Embodiment

The rear-end transmission device of the surgical robot according to the second embodiment of the present disclosure will be described in detail below with reference to FIGS. 4 and 5. The rear-end transmission device according to the second embodiment has substantially the same structure as the rear-end transmission device 150 according to the first embodiment, in which structures having the same or similar functions are given similar reference numerals.

Figure 4:
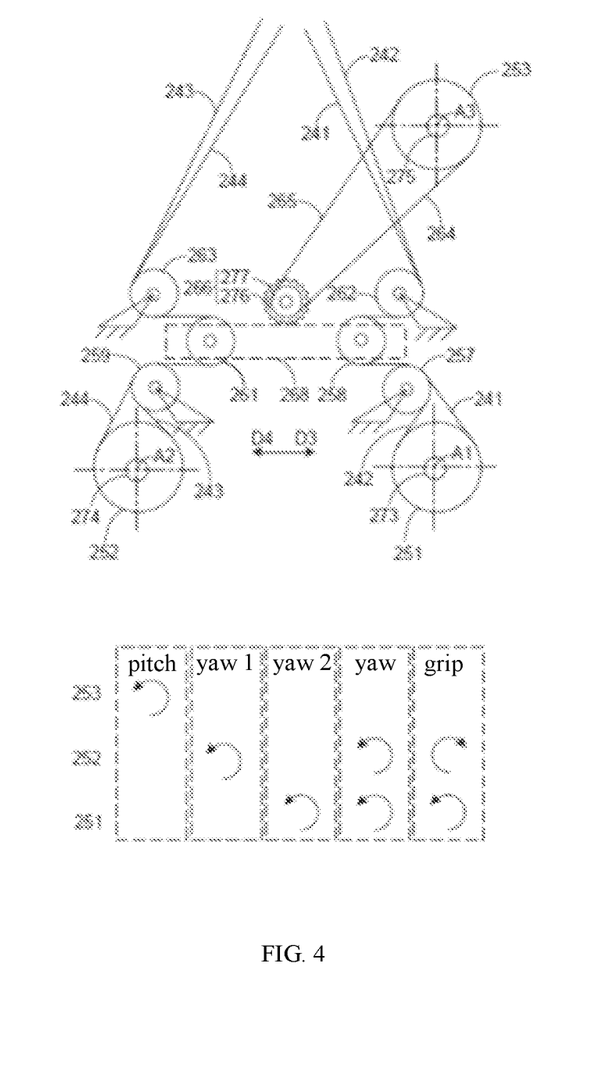
FIG. 4 is a schematic partial structural view of a surgical robot according to a second embodiment of the present disclosure including a rear-end transmission device.
Figure 5:
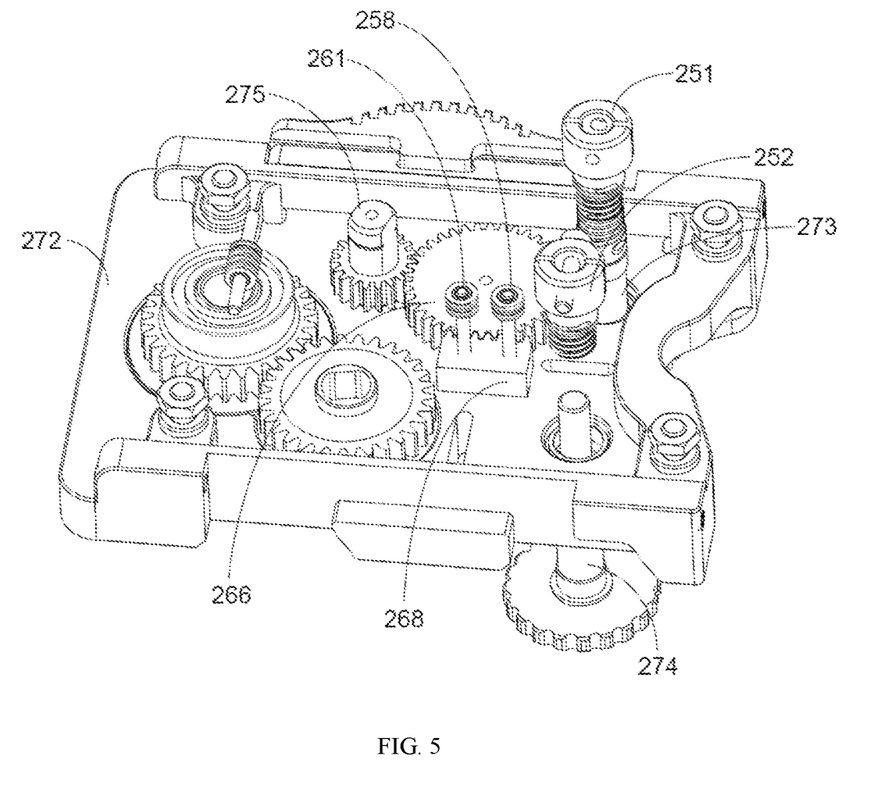
FIG. 5 is another schematic partial structural view of the surgical robot of FIG. 4.

Similar to the first embodiment, as shown in FIGS. 4 and 5, the rear-end transmission device of the second embodiment also includes a first rotating member 251, a second rotating member 252, a first pulley assembly, a second pulley assembly, a position adjusting assembly, a first rotating shaft 273, a second rotating shaft 274, and a third rotating shaft 275. The first pulley assembly also includes a first guide pulley 257, a first movable pulley 258, and a third guide pulley 262. The second pulley assembly also includes a second guide pulley 259, a second movable pulley 261, and a fourth guide pulley (e.g., fixed pulley) 263. The position adjusting assembly also includes a third rotating member 253. Details of those may be referred to the above description of the first embodiment and will not be repeated hereafter for the sake of brevity.

The rear-end transmission device includes a chassis 272. Each of the first rotating shaft 273, the second rotating shaft 274, and the third rotating shaft 275 is rotatably mounted to the chassis 272. The first pulley assembly, the second pulley assembly, and the position adjusting assembly are mounted to the chassis 272. The chassis 272 has at least one interface, and each of the at least one interface corresponds to a respective port of the robotic arm, which may ensure that each of the first rotating shaft 273, the second rotating shaft 274, and the third rotating shaft 275 can be stably connected to the driving motor at a corresponding docking port of the robotic arm when the surgical instrument is properly mounted, so as to realize the transmission of rotational motion.

Different from the first embodiment, in the second embodiment, the position adjusting assembly further includes a first transmission cable 264, a second transmission cable 265, and a rotating assembly 266. The first transmission cable 264 and the second transmission cable 265 each have one end connected to the third rotating member 253 and have the other end connected to the rotating assembly 266. The first transmission cable 264 and the second transmission cable 265 wrap around the third rotating member 253 in opposite directions, and wrap around the rotating assembly 266 in opposite directions. The rotating assembly 266 can be meshed with the slider 268, and the slider 268 is linearly movable with a rotation of the rotating assembly 266. The arrows in FIG. 4 show moving directions D3 and D4 of the slider 268, where the direction D4 is opposite to the direction D3. In an embodiment, the moving directions D3 and D4 of the slider 268 are substantially horizontal. It shall be understood that the moving direction of the slider 268 may be selected as desired. For example, the moving directions D3 and D4 of the slider 268 may also be substantially vertical or may also be at an angle to the horizontal.

Specifically, the rotating assembly 266 is rotatable around an axis substantially parallel to the third central axis A3. The rotating assembly 266 includes a gear 276 and a pulley 277 that is synchronously rotated with the gear 276. The other end of the first transmission cable 264 and the other end of the second transmission cable 265 are connected to the pulley 277, respectively. The first transmission cable 264 and the second transmission cable 265 wrap around the pulley 277 in opposite directions. The slider 268 is a rack meshed with the gear 276.

When the third rotating shaft 275 is controlled by the driving motor to drive the third rotating member 253 to rotate counterclockwise, the first transmission cable 264 is pulled in and the second transmission cable 265 is released in equal lengths concurrently, to pull the slider 268, the first movable pulley 258, and the second movable pulley 261 to move in the direction D3. Therefore, the first cable 241 and the second cable 242 are released in equal lengths and the third cable 243 and the fourth cable 244 are pulled in in equal lengths concurrently, where a total length of released portions of the first cable and the second cable is equal to a total length of pulled-in portions of the third cable and the fourth cable, thereby realizing pitch of the wrist mechanism in a direction. Similarly, when the third rotating shaft 275 is controlled by the driving motor to drive the third rotating member 253 to rotate clockwise, the first transmission cable 264 is released and the second transmission cable 265 is pulled in in equal lengths concurrently, to pull the slider 268, the first movable pulley 258, and the second movable pulley 261 to move in the direction D4. Therefore, the first cable 241 and the second cable 242 are pulled in in equal lengths and the third cable 243 and the fourth cable 244 are released in equal lengths concurrently, where a total length of pulled-in portions of the first cable and the second cable is equal to a total length of released portions of the third cable and the fourth cable, thereby realizing the pitch of the wrist mechanism in a reverse direction.

Third Embodiment

The rear-end transmission device of the surgical robot according to the third embodiment of the present disclosure will be described in detail below with reference to FIG. 6. The rear-end transmission device according to the third embodiment has substantially the same structure as the rear-end transmission device according to the second embodiment, in which structures having the same or similar functions are given similar reference numerals.

Figure 6:
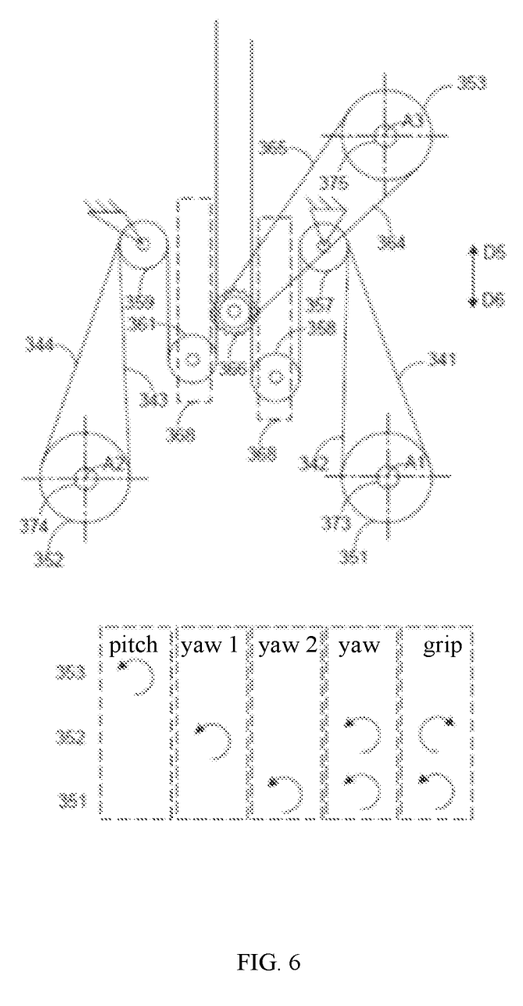
FIG. 6 is a schematic partial structural view of a surgical robot according to a third embodiment of the present disclosure including a rear-end transmission device.

Similar to the second embodiment, as shown in FIG. 6, the rear-end transmission device of the third embodiment also includes a first rotating member 351, a second rotating member 352, a first pulley assembly, a second pulley assembly, a position adjusting assembly, a first rotating shaft 373, a second rotating shaft 374, and a third rotating shaft 375. The position adjusting assembly also includes a third rotating member 353. Details of those may also be referred to the above description of the first and the second embodiments and will not elaborated hereafter for the sake of brevity.

Different from the second embodiment, the first pulley assembly of the third embodiment includes a first guide pulley 357 and a first movable pulley 358. Each of a first cable 341 and a second cable 342 extends from the first rotating member 351 and rides on the first guide pulley 357 and the first movable pulley 358 sequentially. The second pulley assembly includes a second guide pulley 359 and a second movable pulley 361. Each of a third cable 343 and a fourth cable 344 extends from the second rotating member 352 and rides on the second guide pulley 359 and the second movable pulley 361 sequentially.

In the embodiments of the disclosure, the position adjusting assembly includes a pair of substantially parallel sliders 368 spaced apart from each other. Each of the first movable pulley 358 and the second movable pulley 361 is rotatably connected to a respective one of the pair of sliders 368. A rotating assembly 366 is provided and disposed between the pair of sliders 368 and is meshed with the pair of sliders 368 in such a way that the pair of sliders 368 can move in opposite directions. Arrows in FIG. 6 show moving directions D5 and D6 of each of the sliders 368, where the direction D6 is opposite to the direction D5. In an embodiment, the moving directions D5 and D6 of the slider 368 are substantially horizontal. It shall be understood that the moving direction of the slider 368 may be selected as required. For example, the moving directions D5 and D6 of the slider 368 may also be substantially vertical or may also be at an angle to the horizontal.

When the third rotating shaft 375 is controlled by the driving motor to drive the third rotating member 353 to rotate counterclockwise, the first transmission cable 364 is pulled in and the second transmission cable 365 is released in equal lengths concurrently, so that one slider 368 on which the first movable pulley 358 is disposed is moved in the direction D5, and the other slider 368 on which the second movable pulley 361 is disposed is moved in the direction D6. Therefore, the first cable 341 and the second cable 342 are released in equal lengths and the third cable 343 and the fourth cable 344 are pulled in in equal lengths concurrently, where a total length of released portions of the first cable and the second cable is equal to a total length of pulled-in portions of the third cable and the fourth cable, thereby realizing pitch of the wrist mechanism in a direction. Similarly, when the third rotating shaft 375 is controlled by the driving motor to drive the third rotating member 353 to rotate clockwise, the first transmission cable 364 is released and the second transmission cable 365 is pulled in in equal lengths concurrently, so that the one slider 368 on which the first movable pulley 358 is disposed is moved in the direction D6, and the other slider 368 on which the second movable pulley 361 is disposed is moved in the direction D5. Therefore, the first cable 341 and the second cable 342 are pulled in in equal lengths and the third cable 343 and the fourth cable 344 are released in equal lengths concurrently, where a total length of pulled-in portions of the first cable and the second cable is equal to a total length of released portions of the third cable and the fourth cable, thereby realizing pitch of the wrist mechanism in a reverse direction.

According to embodiments of the present disclosure, the rear-end transmission device is connected to four driving cables (i.e., the first cable, the second cable, the third cable, and the fourth cable) of the wrist mechanism, such that the wrist mechanism works cooperatively with the rear-end transmission device, to achieve pitch, yaw, and grip of the wrist mechanism by pulling in or releasing the driving cables. The rotation of the lower claw and the upper claw, i.e., the yaw and the grip of the effector of the wrist mechanism, can be realized by reversely driving the two driving cables (i.e., the first cable and the second cable) connected to the lower claw of the effector of the wrist mechanism in equal lengths and reversely driving the two driving cables (i.e., the third cable and the fourth cable) connected to the upper claw in equal lengths. The pitch of the wrist mechanism can be realized by reversely driving the two driving cables (i.e., pulling in or releasing the first cable and the second cable concurrently) connected to the lower claw and the two driving cables (i.e., releasing or pulling in the third cable and the fourth cable concurrently) connected to the upper claw respectively in equal lengths. The linear-combination driving is realized by means of a plurality of movable pulleys (i.e., the first movable pulley and the second movable pulley), three driving shafts (i.e., the first rotating shaft, the second rotating shaft, and the third rotating shaft), and three rotating members (i.e., the first rotating member, the second rotating member, and the third rotating member), which is accurate in transmission. Furthermore, a rotation angle of the rotating member is linearly related to a pitch angle, a yaw angle, and a grip angle of the wrist mechanism respectively, and therefore, equal-length release and/or pulling-in of the driving cables can be ensured even when the above-mentioned angles of the wrist mechanism vary in a wide range.

Unless otherwise defined, technical and scientific terms used herein have the same meanings as are commonly understood by those skilled in the art of the present disclosure. Terms used herein are for specific practical purposes only and are not intended to limit the present disclosure. Terms such as "disposed/disposing" that appear herein may denote either a part is attached directly to another part or a part is attached to another part through middleware. Features described herein in one embodiment may be applied to another embodiment alone or in combination with other features unless the features are not applicable in the other embodiment or otherwise noted.

The present disclosure has been described by way of the above-described embodiments but it shall be understood that the above-described embodiments are for the purpose of illustrative and illustration only and are not intended to limit the present disclosure to the scope of the described embodiments. Those skilled in the art will appreciate that many more variations and modifications may be made according to the teachings of the present disclosure, all of which fall within the scope of the claims of the present disclosure.

What is claimed is:

1. A rear-end transmission device, comprising:
   a first rotating member connected to a first cable and a second cable, wherein the first cable and the second cable wrap around the first rotating member in opposite directions;
   a second rotating member connected to a third cable and a fourth cable, wherein the third cable and the fourth cable wrap around the second rotating member in opposite directions;
   a first pulley assembly including a first movable pulley, wherein each of the first cable and the second cable extends from the first rotating member and rides on the first movable pulley;
   a second pulley assembly including a second movable pulley, wherein each of the third cable and the fourth cable extends from the second rotating member and rides on the second movable pulley; and
   a position adjusting assembly connected to the first movable pulley and the second movable pulley, and configured to concurrently adjust positions of the first movable pulley and the second movable pulley, to perform one of: pulling in the first cable and the second cable while releasing the third cable and the fourth cable, and pulling in the third cable and the fourth cable while releasing the first cable and the second cable.

2. The rear-end transmission device of claim 1, wherein the first rotating member is rotatable around a first central axis of the first rotating member to perform via the first pulley assembly: pulling in one of the first cable and the second cable while releasing another of the first cable and the second cable; and
   the second rotating member is rotatable around a second central axis of the second rotating member to perform via the second pulley assembly: pulling in one of the third cable and the fourth cable while releasing another of the third cable and the fourth cable.

3. The rear-end transmission device of claim 2, wherein the first central axis is substantially parallel to the second central axis, each of the first movable pulley and the second movable pulley is rotatable around a respective axis substantially parallel to the first central axis, and the axis of the first movable pulley and the axis of the second movable pulley are spaced apart from each other.

4. The rear-end transmission device of claim 3, wherein the first pulley assembly further comprises a first guide pulley and a third guide pulley, each of the first guide pulley and the third guide pulley is rotatable around a respective axis substantially parallel to the first central axis, and each of the first cable and the second cable extends from the first rotating member and sequentially rides on the first guide pulley, the first movable pulley, and the third guide pulley.

5. The rear-end transmission device of claim 3, wherein the second pulley assembly further comprises a second guide pulley and a fourth guide pulley, each of the second guide pulley and the fourth guide pulley is rotatable around a respective axis substantially parallel to the second central axis, and each of the third cable and the fourth cable extends from the second rotating member and sequentially rides on the second guide pulley, the second movable pulley, and the fourth guide pulley.

6. The rear-end transmission device of claim 3, wherein the position adjusting assembly comprises a third rotating member, and the third rotating member is rotatable around a third central axis, of the third rotating member, substantially parallel to the first central axis, to concurrently adjust the positions of the first movable pulley and the second movable pulley.

7. The rear-end transmission device of claim 6, wherein the position adjusting assembly further comprises a slider, each of the first movable pulley and the second movable pulley is rotatably connected to the slider, and the third rotating member is configured to adjust a position of the slider.

8. The rear-end transmission device of claim 7, wherein the position adjusting assembly further comprises a first transmission cable, a second transmission cable, a fifth guide pulley, and a sixth guide pulley, wherein
the first transmission cable rides on the fifth guide pulley; and
the second transmission cable rides on the sixth guide pulley, wherein the first transmission cable and the second transmission cable each have one end connected to the third rotating member and wrap around the third rotating member in opposite directions, and wherein the first transmission cable has another end connected to one end of the slider and the second transmission cable has another end connected to another end of the slider.

9. The rear-end transmission device of claim 8, wherein the fifth guide pulley and the sixth guide pulley each are rotatable around a respective axis substantially parallel to the third central axis, and the axis of the fifth guide pulley and the axis of the sixth guide pulley are spaced apart from each other.

10. The rear-end transmission device of claim 7, wherein the position adjusting assembly further comprises a first transmission cable, a second transmission cable, and a rotating assembly, wherein
the first transmission cable and the second transmission cable each have one end connected to the third rotating member and wrap around the third rotating member in opposite directions;
the first transmission cable and the second transmission cable each have another end connected to the rotating assembly and wrap around the rotating assembly in opposite directions; and
the rotating assembly is meshed with the slider, and the slider is linearly movable with a rotation of the rotating assembly.

11. The rear-end transmission device of claim 10, wherein the rotating assembly is rotatable around an axis substantially parallel to the third central axis, the rotating assembly includes a gear, and the slider is a rack meshed with the gear.

12. The rear-end transmission device of claim 10, wherein the position adjusting assembly includes a pair of substantially parallel sliders, wherein each of the first movable pulley and the second movable pulley is rotatably connected to a respective one of the pair of sliders, and the rotating assembly is disposed between the pair of sliders and is meshed with the pair of sliders to enable the pair of sliders to move in opposite directions.

13. A surgical instrument, comprising a rear-end transmission device, wherein the rear-end transmission device comprises:
a first rotating member connected to a first cable and a second cable, wherein the first cable and the second cable wrap around the first rotating member in opposite directions;
a second rotating member connected to a third cable and a fourth cable, wherein the third cable and the fourth cable wrap around the second rotating member in opposite directions;
a first pulley assembly including a first movable pulley, wherein each of the first cable and the second cable extends from the first rotating member and rides on the first movable pulley;
a second pulley assembly including a second movable pulley, wherein each of the third cable and the fourth cable extends from the second rotating member and rides on the second movable pulley; and
a position adjusting assembly connected to the first movable pulley and the second movable pulley, and configured to concurrently adjust positions of the first movable pulley and the second movable pulley, to perform one of: pulling in the first cable and the second cable while releasing the third cable and the fourth cable, and pulling in the third cable and the fourth cable while releasing the first cable and the second cable.

14. The surgical instrument of claim 13, wherein
the first rotating member is rotatable around a first central axis of the first rotating member to perform via the first pulley assembly: pulling in one of the first cable and the second cable while releasing another of the first cable and the second cable; and
the second rotating member is rotatable around a second central axis of the second rotating member to perform via the second pulley assembly: pulling in one of the third cable and the fourth cable while releasing another of the third cable and the fourth cable.

15. The surgical instrument of claim 14, wherein the first central axis is substantially parallel to the second central axis, each of the first movable pulley and the second movable pulley is rotatable around a respective axis substantially parallel to the first central axis, and the axis of the first movable pulley and the axis of the second movable pulley are spaced apart from each other.

16. The surgical instrument of claim 15, wherein the first pulley assembly further comprises a first guide pulley and a third guide pulley, each of the first guide pulley and the third guide pulley is rotatable around a respective axis substantially parallel to the first central axis, and each of the first cable and the second cable extends from the first rotating member and sequentially rides on the first guide pulley, the first movable pulley, and the third guide pulley.

17. The surgical instrument of claim 15, wherein the second pulley assembly further comprises a second guide pulley and a fourth guide pulley, each of the second guide pulley and the fourth guide pulley is rotatable around a respective axis substantially parallel to the second central axis, and each of the third cable and the fourth cable extends from the second rotating member and sequentially rides on the second guide pulley, the second movable pulley, and the fourth guide pulley.

18. The surgical instrument of claim 15, wherein the position adjusting assembly comprises a third rotating member, and the third rotating member is rotatable around a third central axis, of the third rotating member, substantially parallel to the first central axis, to concurrently adjust the positions of the first movable pulley and the second movable pulley.

19. The surgical instrument of claim 18, wherein the position adjusting assembly further comprises a slider, each of the first movable pulley and the second movable pulley is rotatably connected to the slider, and the third rotating member is configured to adjust a position of the slider.

20. A surgical robot, comprising a surgical instrument, wherein the surgical instrument comprises a rear-end transmission device comprising:
- a first rotating member connected to a first cable and a second cable, wherein the first cable and the second cable wrap around the first rotating member in opposite directions;
- a second rotating member connected to a third cable and a fourth cable, wherein the third cable and the fourth cable wrap around the second rotating member in opposite directions;
- a first pulley assembly including a first movable pulley, wherein each of the first cable and the second cable extends from the first rotating member and rides on the first movable pulley;
- a second pulley assembly including a second movable pulley, wherein each of the third cable and the fourth cable extends from the second rotating member and rides on the second movable pulley; and
- a position adjusting assembly connected to the first movable pulley and the second movable pulley, and configured to concurrently adjust positions of the first movable pulley and the second movable pulley, to perform one of: pulling in the first cable and the second cable while releasing the third cable and the fourth cable, and pulling in the third cable and the fourth cable while releasing the first cable and the second cable.

* * * * *